(12) United States Patent
Michejda et al.

(10) Patent No.: US 6,187,775 B1
(45) Date of Patent: Feb. 13, 2001

(54) ACRIDONE-DERIVED COMPOUNDS USEFUL AS ANTINEOPLASTIC AND ANTIRETROVIRAL AGENTS

(75) Inventors: Christopher J. Michejda, Potomac; Marek W. Cholody, Frederick; William G. Rice, Frederick; James A. Turpin, Frederick, all of MD (US)

(73) Assignee: The United States of America as represented by the Department of Health and Human Services, Washington, DC (US)

( * ) Notice: Under 35 U.S.C. 154(b), the term of this patent shall be extended for 0 days.

(21) Appl. No.: 09/155,141

(22) PCT Filed: Apr. 9, 1997

(86) PCT No.: PCT/US97/07070

§ 371 Date: Sep. 22, 1998

§ 102(e) Date: Sep. 22, 1998

(87) PCT Pub. No.: WO97/38999

PCT Pub. Date: Oct. 23, 1997

Related U.S. Application Data

(60) Provisional application No. 60/015,326, filed on Apr. 12, 1996, and provisional application No. 60/035,050, filed on Jan. 22, 1997.

(51) Int. Cl.[7] .......................... A61K 31/497; A61P 35/00; C07D 401/14
(52) U.S. Cl. ................... 514/253.02; 514/253.03; 544/361
(58) Field of Search ................... 514/253, 253.02, 514/253.03; 544/361

(56) References Cited

FOREIGN PATENT DOCUMENTS

0502668 * 9/1992 (EP) .
95/25093 * 9/1995 (WO) .

OTHER PUBLICATIONS

Cholody, W.M. et al. Bisimiazoacridones and Related Compounds: New Antineoplastic Agents with High Selectivity against Colon Tumors. Journal of Medicinal Chemistry. vol. 38 (1995): pp. 3043–3052.*

Hernandez, L. et al. Mechanism of Action of Bisimidazoacridones, New Drugs with Potent Selective Activity against Colon Cancer. Cancer Research. vol. 55 (Jun. 1995): pp. 2338–2345.*

* cited by examiner

Primary Examiner—Michael G. Ambrose

(74) Attorney, Agent, or Firm—Morgan & Finnegan, L.L.P.; William S. Feiler; Dorothy R. Auth

(57) ABSTRACT

The present invention relates to several novel acridone-derived compounds of of formula (I) or (II). These compounds are potent anti-viral agents, useful in the treatment of viral diseases, such as Human Immunodeficiency Virus. In addition, these compounds are anti-neoplastic agents useful in the treatment of various forms of cancer.

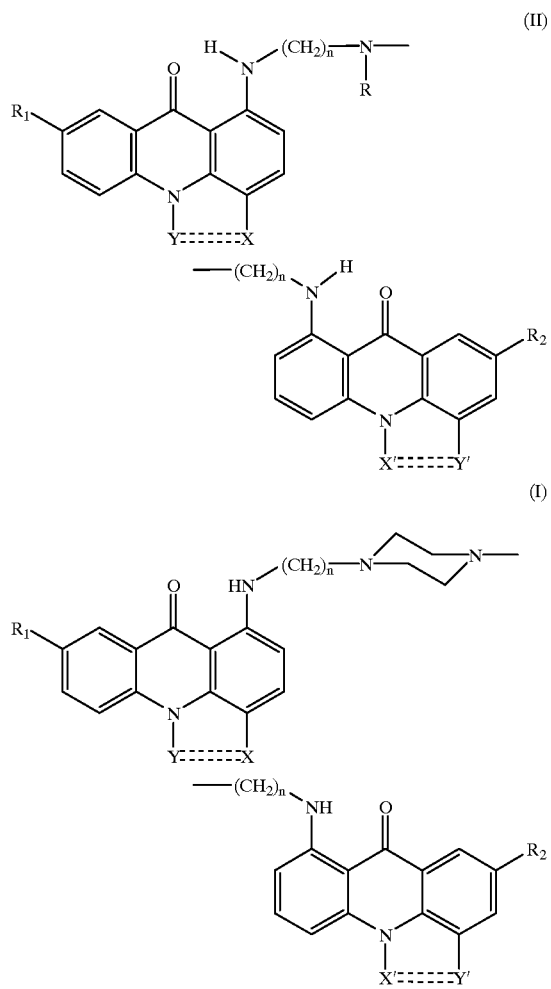

wherein R1 and R2 are independently —H, —OH, amino, alkylamino, dialkylamino, alkoxy, alkyl, haloalkyl or halogen; n is 2 to 6, X and X' are independently —N or —NO$_2$; Y and Y' are independently —N or —CH, or —H; and the double-slash represents a double bond or no bond.

5 Claims, 13 Drawing Sheets

ACRIDONE-DERIVED COMPOUNDS USEFUL AS ANTINEOPLASTIC AND ANTIRETROVIRAL AGENTS

This application was filed under 35 U.S.C. 371 and is the National Stage of PCT International Application No. PCT/US97/07070, filed Apr. 9, 1997, which claims the benefit of U.S. provisional application Ser. Nos. 60/015,326 and 60/035,050; filed Apr. 12, 1996 and Jan. 22, 1997, respectively.

FIELD OF THE INVENTION

The present invention relates to acridone-derived compounds which are bisimidazoacridones, bistriazoloacridones and hybrid molecules having both imidazoacridone and triazoloacridone moieties. These compounds are useful as anti-neoplastic and anti-retroviral agents.

BACKGROUND OF THE INVENTION

A number of acridine-based compounds which exhibit high antitumor activity recently have been reported. Cholody W. M., et al. (1990) described 5-[(Aminoalkly)amino] imidazo[4,5,1-de]acridin-6-ones as a novel class of antineoplastic agents (*J. Med. Chem.* 33:49–52 (1990). 8-Substituted 5-[(aminoalkyl)amino]-6H-v-triazolo[4,5,1-de]acridin-6-ones have also been described as potential antineoplastic agents (*J. Med. Chem.* 33:2852–2856 (1990)). The synthesis of chromophobe modified antineoplastic imidazaoacridones and their activity against murine leukemias has been described (*J. Med. Chem.* 35:378–382 (1992)). Capps, D. B., et al. described 2-(aminoalkyl)-5-nitropyrazolo[3,4, 5-kl] acridones as a new class of anticancer agents (*J. Med. Chem.* 35:4770–4778 (1992)).

The above compounds have a tetracyclic planar chromophore bearing one side chain containing an (aminoalkyl) amino residue as a common structural feature. It is believed that DNA is the primary target for these compounds and that they bind to DNA by intercalation.

Bifunctional compounds also have been studied as potential antitumor agents based upon the ability of acridones and other planar aromatic compounds to interact with DNA by intercalation. Chen, T. K., et al. (1978) studied diacridines as bifunctional intercalators (*J. Med. Chem.* 21:868–874 (1978)). Gaugain, B., et al. (1978) described the synthesis and conformational properties of an ethidium homodimer and an acridine ethidium heterodimer (Biochemistry 17:5071–5078 (1978)). Sinha, B. K., et al. (Biochemistry 17:5071–5078 (1977)) described the synthesis and antitumor properties of bis(quinaldine) derivatives (J. Med. Chem.20:1528–1531 (1977)). Roques, B. P., et al. (1979) described the antileukemic activity of pyridocarbazole dimers (Biochem. Pharmacol 28:1811–1815 (1979)). Pelaprat, D. et al. (1980) described 7H-pyridocarbazole dimers as potential antitumor agents (J. Med. Chem. 23:1336–1343 (1980)). Brana, M. F., et al. (1993) described bis-naphtalimides as a class of antitumor agents (*Anti-Cancer Drug Design* 8:257–268 (1993)).

The rationale for the strong binding of bifunctional intercalators containing two aromatic ring systems joined by a suitable linker to nucleic acids has been presented (Canellakis, E. S., et al. *Biochem Biophys. Acta* 418:277–283 (1976). It was found that although such compounds exhibit high affinity for DNA, this strong binding with DNA by intercalation is generally not related to antitumor activity.

Many factors, such as physicochemical characteristics of the planar chromophores, nature of the linking chain (its length, rigidity and ionization state), position of attachment, and other factors, strongly influence the binding with DNA and the biological action of these compounds. Additionally, it was found that there is no direct correlation between DNA-binding affinity and cytotoxicity.

Since structure-activity relationships in the group of bifunctional intercalators in relation to their in vivo antitumor action remain unclear, it is not possible to predict structures that will show such activity. Small structural modifications can drastically change biological properties of the agent. Accordingly, a goal exists to find other compounds with high antineoplastic activity, especially selectively directed towards specific tumors.

It was previously disclosed that certain bisimidazoacridones, the closely related bistriazoloacridones and hybrid molecules containing both the imidazoacridone and triazoloacridone moieties were potent but selective antitumor agents (U.S. Pat. No. 5,508,289).

This invention relates to a novel class of acridine-based compounds and their use as antineoplastic agents and as antiretroviral agents. It has further been found that the bismidazocridones, the bistriazoloacridones and hybrid molecules disclosed in U.S. Pat. No. 5,508,289 are useful as antiretroviral agents.

SUMMARY OF THE INVENTION

The present invention relates to compounds having the following general formula (I):

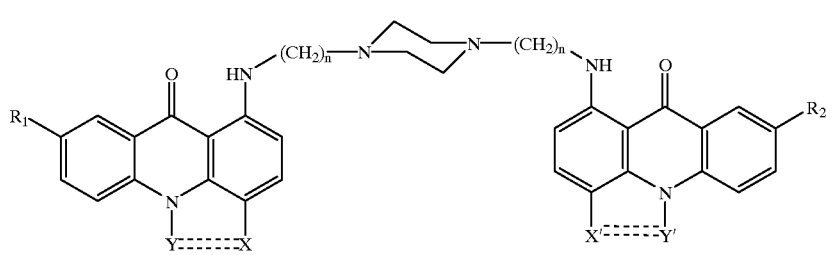

(I)

wherein R1 and R2 are independently —H, —OH, amino, alkylamino, dialkylamino, alkoxy, alkyl, haloalkyl or halogen; n is 2 to 6, X and X' are independently —N or —N$_2$; Y and Y' are independently —N or —CH, or —H; and the double-slash represents a double bond or no bond; such that when X or X' is —N, Y or Y' is —CH or —N, and the double-slash is a double bond, and when X or X' is —NO$_2$, Y or Y' is —H, and the double slash is no bond.

The present invention also provides a pharmaceutical composition comprising at least one of the above compounds and a pharmaceutically acceptable carrier.

The present invention further provides a method for treating a neoplastic cell growth in a subject in need of such treatment which comprises administering to the subject an amount of the pharmaceutical composition above effective to treat the neoplastic cell growth.

The present invention still further provides a method for treating retroviral infections in a population of cells including human cells comprising contacting the cell population or administering to a subject having retroviral infected cells an effective amount of at least one compound of the formula (I).

Also included within the scope of the present invention is a method for protecting a population of cells including human cells against retroviral pathogenesis comprising contacting or treating said cells with an anti-retroviral effective amount of at least one compound according to formula (I).

A yet still further aspect of the present invention provides a method of treating retroviral infections in a population of cells including human cells comprising administering and/or contacting the cells of a subject having retroviral infected cells an effective amount of at least one compound of formula (II):

FIG. 11. Actions of temacrazine in the U1 Assay.

FIG. 12. Effect of temacrazine on the production and processing of viral proteins.

FIG. 13. Temacrazine inactivation of the infectious titer of intact HIV-1 virions.

FIG. 14. Failure of temacrazine to non-specifically inhibit HIV-1 LTR-directed transcription.

FIG. 15. Temacrazine effect on mRNA expression and splicing in HIV-1 infected cells.

FIG. 16. Temacrazine inhibits HIV-1 specific mRNA creating a "rev independent-like" phenotype.

DETAILED DESCRIPTION OF THE INVENTION

As utilized herein, the term "alkyl", alone or in combination, means a straight-chain or branched-chain alkyl radical containing from 1 to about 8, preferably from 1 to about 6, carbon atoms. Examples of such radicals include methyl, ethyl, n-propyl, isopropyl, n-butyl, isobutyl, sec-butyl, tert-butyl, amyl, isoamyl, hexyl, octyl and the like. The alkyl radical may be optionally substituted by substituents which are set forth hereinbelow. The term "alkoxy", alone or in combination, means an alkyl ether radical

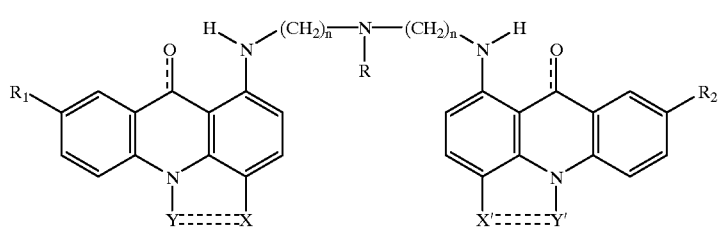

(II)

wherein R is H, alkyl, or a grouping which makes the compound function as a prodrug; n is 2 to 6; and $R_1$, $R_2$, X, Y, X' or Y' and the double dash is as defined hereinabove for formula (I).

Figure 1:
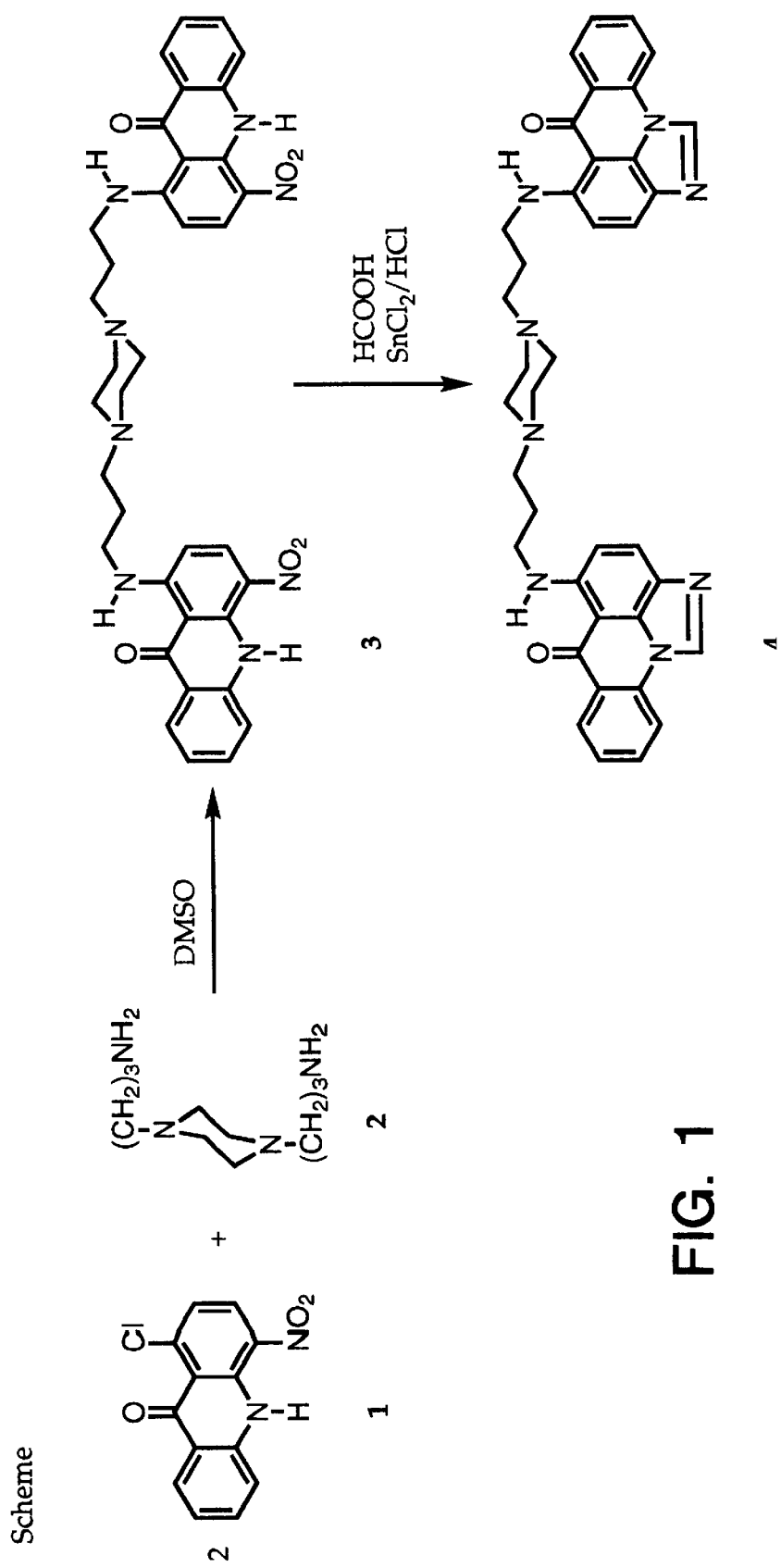
FIG. 1. Schematic showing the preparation of a symmetrical compound.

wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like.

The term "halogen" or "halo" means fluorine, chlorine, bromine or iodine.

The term "haloalkyl" means an alkyl radical having the significance as defined above wherein one or more hydrogens are replaced with a halogen. Examples of such haloalkyl radicals include chloromethyl, 1-bromethyl, fluoromethyl, difluoromethyl, trifluoromethyl, 1,1,1-trifluroethyl and the like.

The possible optional substituents mentioned in the hereinabove generic description include at least one alkyl, cycloalkyl, aryl, aralkyl, alkaryl, heteroaryl, alkoxy, halogen, hydroxy, amino, nitro, cyano, haloalkyl wherein the optional substituents may also be optionally substituted and the radicals which are optionally substituted may be singly or multiply substituted with the same or different optional substituents.

The present invention relates compounds having the general formula I:

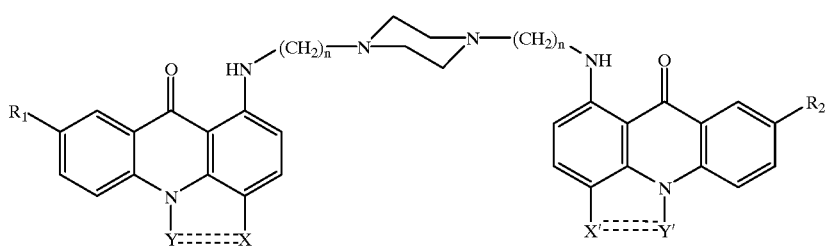

wherein R1 and R2 are each independently —H, —OH, amino, alkylamino, dialkylamino, alkoxy, alkyl, haloalkyl or a halogen atom; n is 2 to 6; X and X and X' are independently —N or —NO$_2$; Y and Y' are independently —N or —CH, or —H; and the double-slash represents a double bond or no bond; such that when X or X' is —N, Y or Y' is —CH or —N, and the double-slash is a double bond, and when X or X' is —NO$_2$, Y or Y' is —H, and the double slash is no bond.

In a preferred embodiment, R1, and R2 are each independently —H, —OH, —NH$_2$, C$_1$–C$_6$ alkylamino, C$_1$–C$_6$ dialkylamino, C$_1$–C$_6$-alkyl, fluorine, chlorine or bromine. A more preferred embodiment includes compounds in which n=3, Y and Y' are —N, X and X' are —CH, R$_1$ and R2 are H, and the double dash is a double bond.

The compounds of the present invention may be employed in the form of free bases or pharmaceutically acceptable acid addition salts thereof. Examples of suitable acids for salt formation are, methanesulfonic, sulfuric, hydrochloric, phosphoric, acetic, citric, lactic, ascorbic, maleic, and the like. In the preferred embodiment, the compounds of the present invention are present in the form of methanesulfonates, such as dimethanesulfonate, or other salts, such as dihydrochloride, which can be hydrated to variable extent. Additionally, the compounds of formulas I and II may be employed in prodrug form. Prodrug forms are known to those skilled in the art and the most effective such form can be determined by the skilled artisan.

The present invention also relates to pharmaceutical compositions comprising at least one of the formula (I) and/or formula (II), and a pharmaceutically acceptable carrier. The carrier must be "acceptable" in the sense of being compatible with the other ingredients of the formulation and not deleterious to the recipient thereof. The compound may be formulated with one or more pharmaceutically acceptable diluents or carriers, and optionally, any other ingredients which may be therapeutic per se, which are synergistic with the compound of the present invention. The concentration of the compound present in the formulation will depend upon the choice of carrier as well as the results desired.

Examples of suitable pharmaceutical carriers include lactose, sucrose, starch, talc, magnesium stearate, crystalline cellulose, methyl cellulose, carboxymethyl cellulose, glycerin, sodium alginate, gum arabic, powders, saline, water, among others. The choice of carrier will depend upon the route of administration. The formulations may conveniently be presented in unit dosage and may be prepared by methods well-known in the pharmaceutical art, by bringing the active compound into association with a carrier or diluent, as a suspension or solution, and optionally one or more accessory ingredients, e.g. buffers, flavoring agents, surface active agents, and the like.

For intravenous, intramuscular, subcutaneous, or intraperitoneal administration, the compound is combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

For oral administration, the formulation may be presented as capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate.

Formulations suitable for parenteral administration conveniently comprise a sterile aqueous preparation of the active compounds which is preferably made isotonic. Preparations for injections may also be formulated by suspending or emulsifying the compounds in non-aqueous solvent, such as vegetable oil, synthetic aliphatic acid glycerides, esters of higher aliphatic acids or propylene glycol.

The present invention further provides a method for treating a neoplastic cell growth in a subject in need of such treatment which comprises administering to the subject an amount of the pharmaceutical composition above effective to treat the neoplastic cell growth.

The term "treatment" includes the partial or total inhibition of neoplastic cell growth or retroviral growth, proliferation and/or spread, as well as the partial or total destruction of the neoplastic cells or retroviruses and/or retrovirally-infected cells. The term "subject" includes a human or animal subject diagnosed as having cancer or a retroviral infection.

The administration may be affected by means known to those skilled in the art such as oral, rectal, topical intravenous, subcutaneous, intramuscular, or intraperitoneal routes of administration.

The dosage form and amount can be readily established by reference to known antineoplastic treatment or prophylactic regimens. In general, however, the dosage of the compound will be within the range of about 0.1 µg/kg to about 100 mg/kg. The actual dose will depend upon the route of administration, the pharmacokinetic and toxicological properties of the individual compound, as well as the results desired.

The compounds of the present invention of formulas I and II are useful in treating retroviral infections in a population of cells including human and animal cells comprising contacting the cell population or administration to a subject having retrovirally infected cells an effective amount of at least one compound of the formulas I and/or II.

The compounds of the present invention including those of formulas I and II may be functional in many retroviral systems to curb the spread of infective virus. Other retroviruses which may be inhibited by the compounds of the present invention include, but are not limited to, HTLV-I, HTLV-II, BLV, EIAV, FIV, SIV, STLV and Visna virus.

Initial experiments involving compounds of formulas I and II revealed that these substances inhibited both the integration and the disintegration steps in an in vitro experiment which utilized the full length purified HIV-1 integrase. These compounds and several others were examined in an anti-viral assay involving peripheral blood lymphocytes which had been infected with HIV-1.

Although the formulations disclosed hereinabove are effective and relatively safe medications for treating HIV infections, the possible concurrent administration of these formulations with other antiviral medications or agents to obtain beneficial results is not excluded. Such other antiviral medications or agents include soluble CD4, thalidomide, dideoxyinosine, dideoxythymine, zidovudine, dideoxycytidine, gancyclovir, acyclovir, phosphonoformate, amatradine, ribavarin, antiviral interferons (e.g. α-interferon, α-interferon, or interleukin-2) or aerosol pentamidine, and other substances used in anti-HIV therapy.

Treatment of infected cells to inhibit virus activity may be for a specific period of time or may be continuous. Virus activity may be measured by monitoring levels of viral protein, such as p24, or by measuring reverse transcriptase levels, or by monitoring virus protein activity by $^{35}$S-met pulse-chase labelling and immunoprecipitation experiments, or by other methods which is a double bond, and when X or X' is —$NO_2$, Y or Y' is —H, and the double slash is no bond are well known by one of skill in the art. (Kayeyama, S., et al. (1994), AIDS *Res. and Human Retroviruses*, 10:735–745).

The present invention is described in the following Experimental Details section, which sets forth specific examples to aid in an understanding of the invention, and should not be construed to limit in any way the invention as defined in the claims which follow thereafter.

EXPERIMENTAL DETAILS SECTION

Materials and Methods. All solvents used were reagent grade. All reagents were obtained either from Aldrich Chemicals or from Fluka and were used as received. Melting points were taken on an Electrothermal capillary melting points apparatus and are uncorrected.

Chemical Synthesis. The compounds of present invention in which both chromophores are identical were prepared by the route presented in FIG. 1. The intermediate chloronitroacridone 1 was prepared as described previously (Capps, D. B., et al. *J. Med. Chem* . 35:4770–4778 (1992); Lehmstedt, K., et al. Chem. Berichte 70:1526–1538 (1937)), or by procedures analogous thereto. The acridone is reacted with an equivalent amount of a suitable piperidine derivative 2 to afford the bisnitroacridone 3, which is then reacted with formic acid and stannous chloride to give the final bisimidazoacridone 4.

Figure 2:
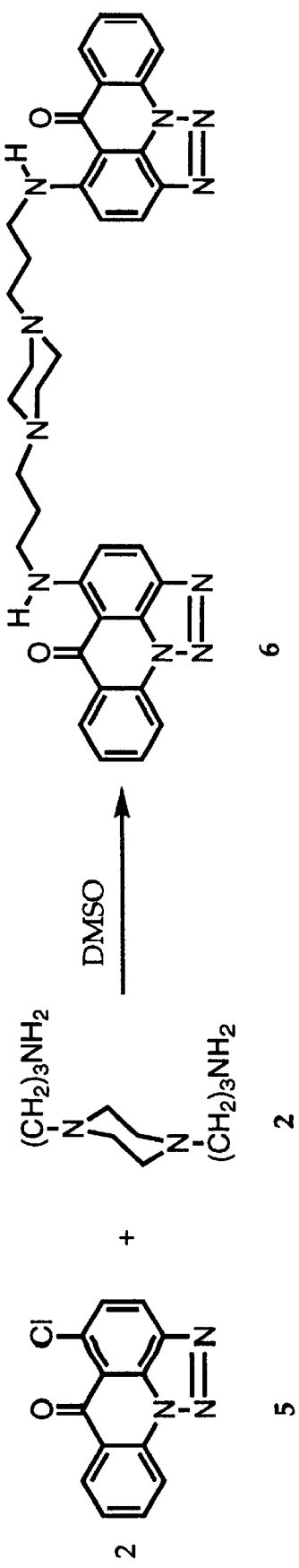
FIG. 2. Schematic showing preparation of a bistriazolo-acridone compound.

Symmetrical drugs of the triazolo series were prepared according to FIG. 2. An acridone is reacted with an excess of piperazine derivative in such a way that the product 7 was formed.

A detailed discussion of the synthesis of the compounds of the present invention is as follows.

EXAMPLE 1

1,4-bis[3[(4-nitro(10H)-9-oxo-acridin-1-yl)amino] propyl]piperazine (3)

A mixture of 1-chloro-4-nitro-9(10H)-acridinone (1) (2.75g, 0.01 mole), 50 mL of DMSO, 1,4bis(3-aminopropyl) piperazine (2) (1.002g, 0.005 mole), and diisopropylethylamine (1.95g, 0.015 mole) was stirred at 80° C. for 8 hours. To the reaction mixture 100 mL of 1% aqueous sodium hydroxide solution was added, stirred for 10 minutes and left overnight in refrigerator. Precipitate was collected by filtration, washed with water and crystallized from DMA to give 2.74g (81%) of yellow (3), mp 274–279° C.(decomp.). Anal. ($C_{36}H_{36}N_8O_6.H_2O$) C, H, N.

1,4-bis[3-[(6-oxo-6H-imidazo [4,5,1-de]-acridin-5-yl)amino]propyl]piperazine (4)

2.03 g (0.003 mole) of (3) was dissolved in 50 mL of 85% formic acid. To the solution a solution of 5.7 g (0.03 mole) of $SnCl_2$ in 6 mL of concentrated hydrochloric acid was added and the mixture was stirred under reflux for 36 hours. After cooling the precipitate was filtered and washed with 50 mL of methanol, transferred into 300 mL of water, and made alkaline with 10% aqueous sodium hydroxide. 30 mL of chloroform-methanol (10:1) mixture was added and stirred vigorously for 2 hours. Undissolved material was filtered off and the chloroform layer was separated. 2 g of silica gel was added to the extract and the solvent was evaporated under vacuo. The gel was then put on a silica gel column and eluted with chloroform-methanol (10:1). The main fraction was collected and after evaporation of solvents gave 1.05g (55%) of yellow (4), mp 289–293° C. (decomp.). Anal. ($C_{38}H_{36}N_8O_2.H_2O$) C, H, N.

1,4-bis[3-[(6-oxo-6H-v-triazolo[4,5,]-de]-acridin-5-yl) (aminopropyl]piperazine (6)

A mixture of 5-chloro-6H-v-triazolo[4,5-de]-acridin-6-one (5) (5.12 g, 0.02 mole), 60 mL of DMSO, 1,4-bis(3-aminopropyl)piperazine (2) (2.003 g, 0.01 mole), and diisopropylethylamine (2.6g, 0.02 mole) was stirred at 100° C. for 20 hours. To the reaction mixture 150 mL of 2% aqueous sodium hydroxide solution was added, stirred thoroughly for 10 minutes and left overnight in a refrigerator. Precipitate was separated by filtration, washed with water, transferred into 200 mL of 1% water solution of methanesulfonic acid and stirred at room temperature for 1 hour. Undissolved material was filtered off. The filtrate was made alkaline with an aqueous solution of sodium hydroxide. The precipitate of the free base was separated by filtration, washed with water and then crystallized twice from boiling DMA to give 3.84 g (60%) of yellow (6), mp 242–245° C. Anal. ($C_{36}_{34}N_{10}O_2.H_2O$) C, H, N. Structure of (6) was confirmed by a single crystal X-ray structure analysis. For biological tests the free bases of (4) and (6) were transformed water-soluble salts such as methanesulfonate or hydrochloride.

EXAMPLE 2

Dihydrochloride of 6

6 (1.2 g, 0.002 mole) was dissolved in boiling mixture of 10% methanol in chloroform (400 mL). To the hot solution, 10 mL of 0.4M hydrochloric acid in methanol(generated by dissolving acetyl chloride in methanol) was added and stirred for few minutes. The solvents were concentrated by evaporation to about 100 mL. 100 mL of ether was added and yellow precipitate of the salt was separated by filtration, washed with ether and dried. Yield—100%, mp>300° C. (decomp.). Anal. ($C_{36}H_{34}N_{10}O_2.2HCl.H_2O$) C, H, N.

Figure 3:
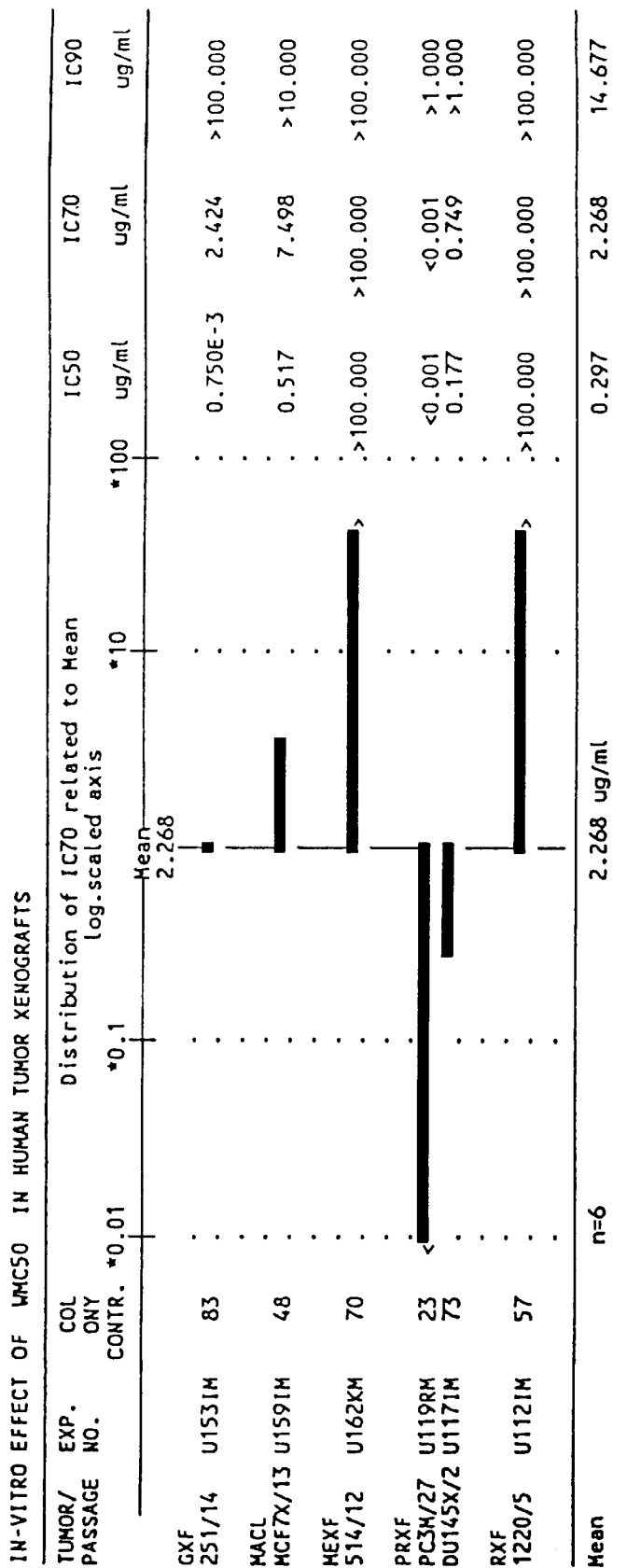
FIG. 3. Anti-tumor activity against human xenografts in vitro.

The activity of compound (4) was tested against several tumor xenografts in vitro. The experiments was carried out on cell lines derived from these tumors, utilizing a standard clonogenic assay protocol. The mean $IC_{70}$ (i.e. the concentration of the chemical which resulted in 70% killing of the tumor cells) for all of the lines tested was 2.3 μg/mL. The gastric carcinoma GFX (251/14) was sensitive at the median dose, but the mammary tumor MACL (MCF7X/13) required over twice the median dose. The melanoma MEXF (514/12) was completely insensitive to the drug, as was the renal carcinoma RXF (1220/5). The prostate cancer cell lines PRXF (PX2M/27 and DU145X/2) were very sensitive to the drug, especially PC3M which required less than 1 nanogram/mL to achieve $IC_{70}$. The results are shown in FIG. 3.

Experiments were performed involving various compounds. These compounds with their alternate designations have the following formulas:

length purified HIV-1 integrase. These compounds and several others were then examined in a cytoprotection assay involving peripheral blood lymphocytes which had been infected with HIV-1.

Briefly, the infected cells in culture are killed by the virus, and the cytotoxicity is detected by the formation of color due to the oxidation of a formazan dye (XTT) by enzymes

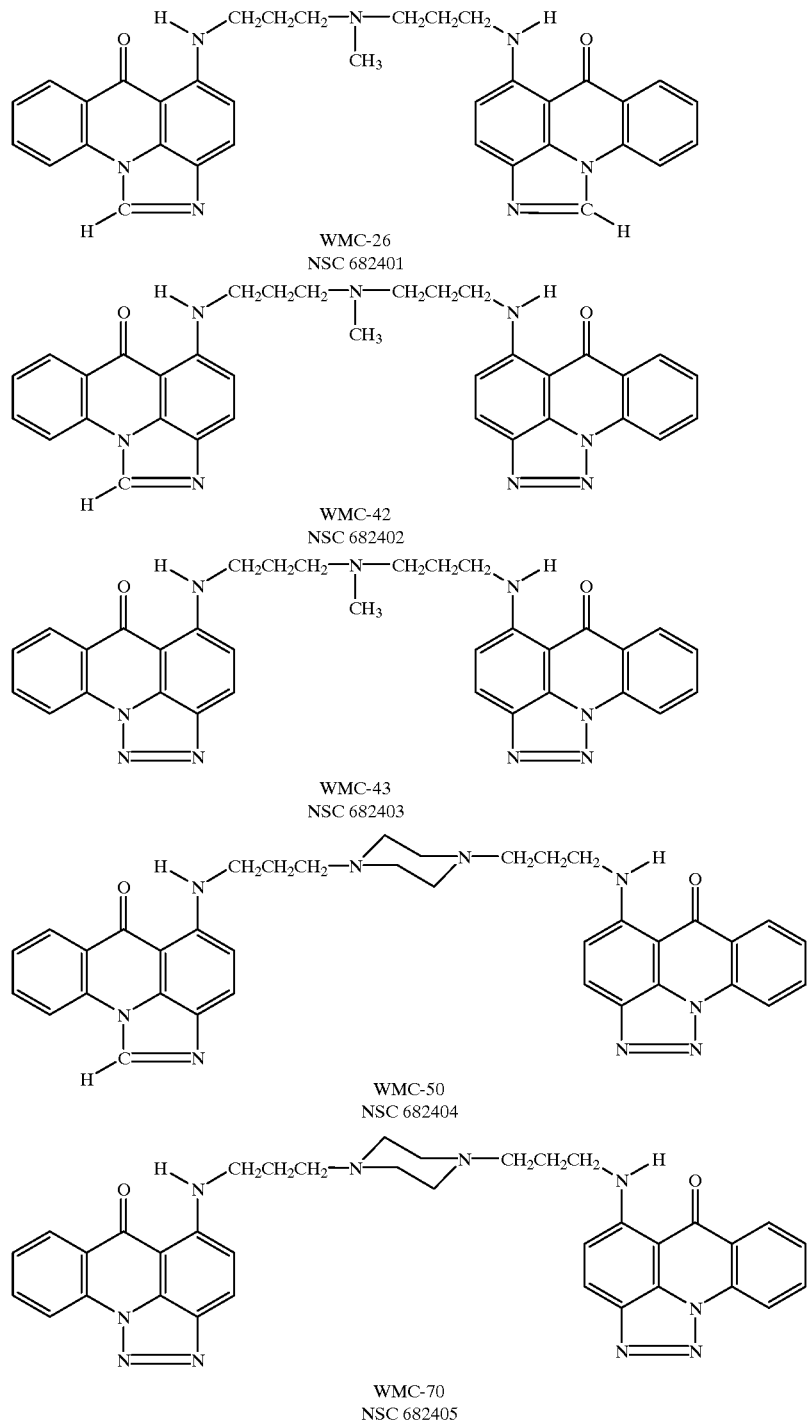

WMC-26
NSC 682401

WMC-42
NSC 682402

WMC-43
NSC 682403

WMC-50
NSC 682404

WMC-70
NSC 682405

Figure 4:
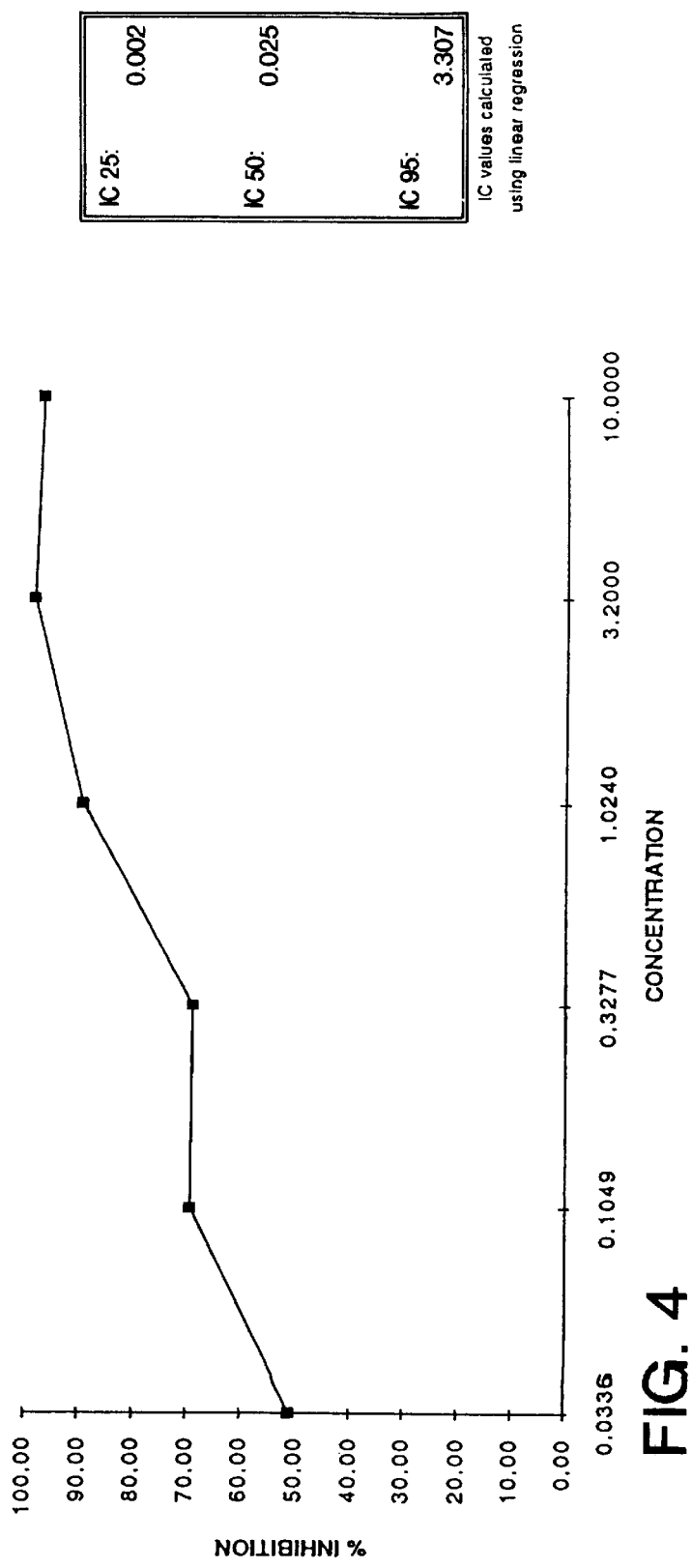
FIG. 4. Cytoprotective activity of WMC-26.
Figure 5:
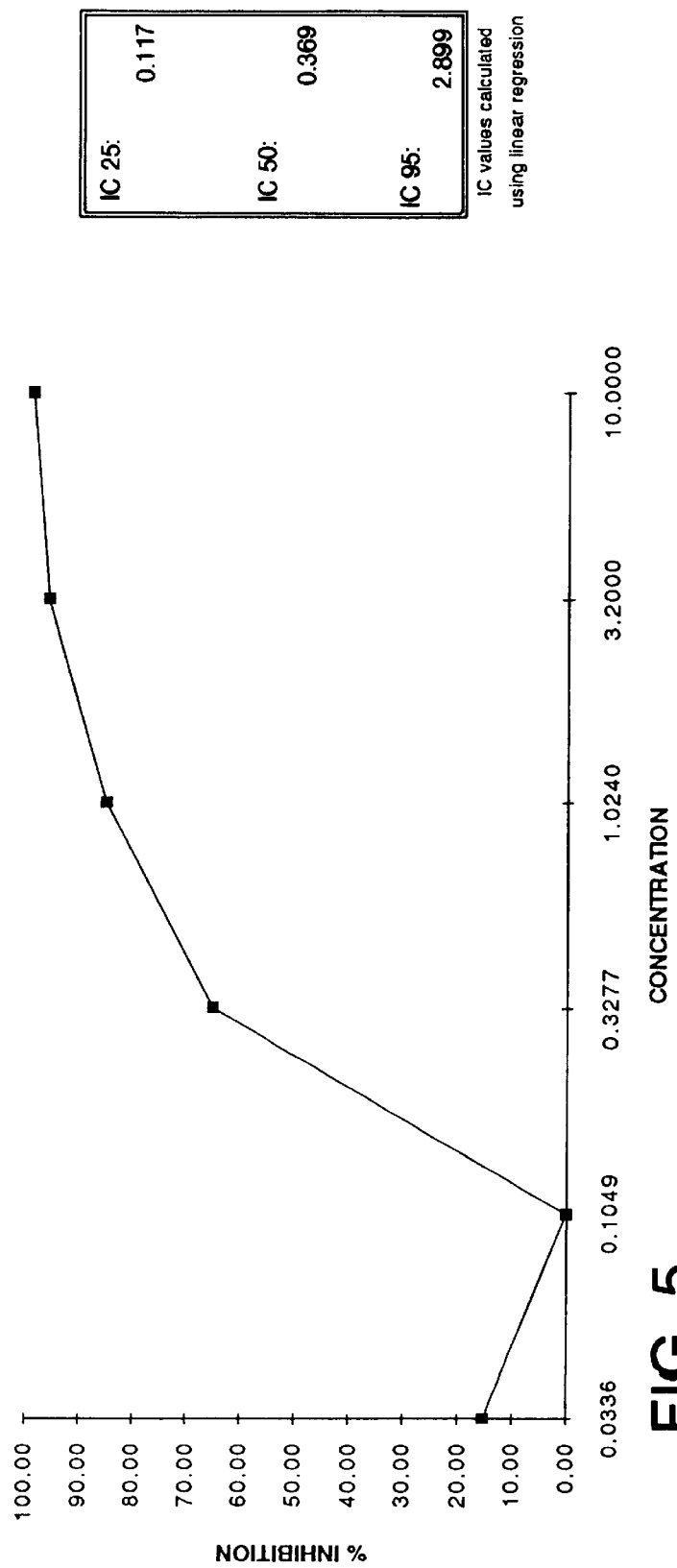
FIG. 5. Cytoprotective activity of WMC-42
Figure 6:
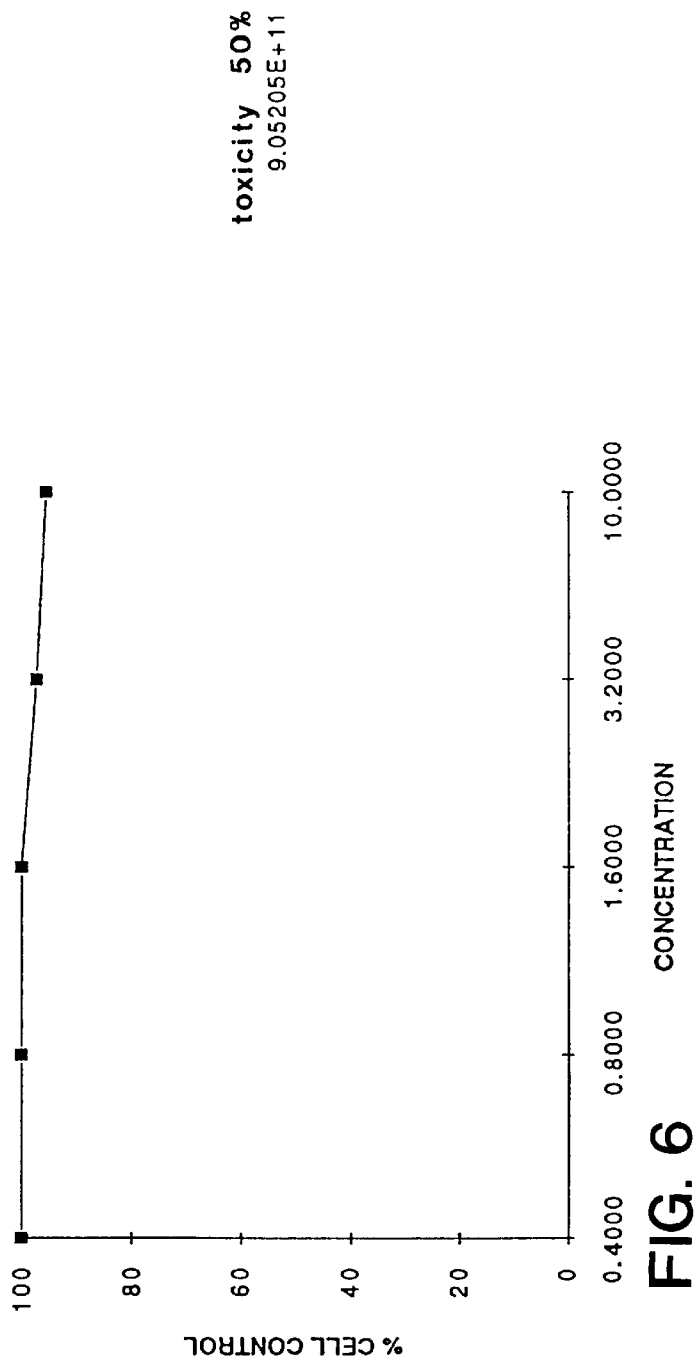
FIG. 6. Parallel experiment with uninfected cells (WMC-26).
Figure 7:
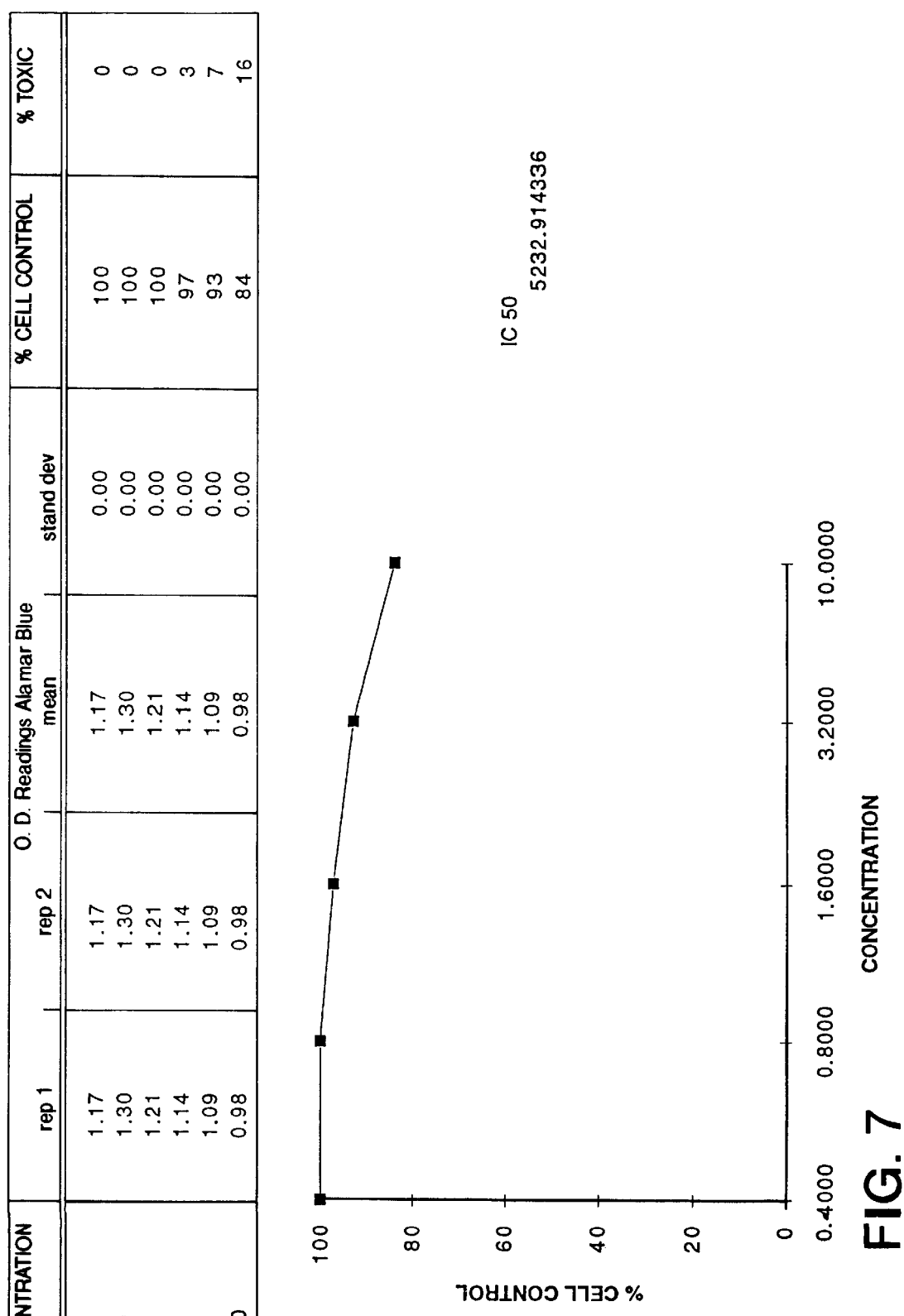
FIG. 7. Parallel experiment with uninfected cells (WMC-42).

Experiments involving WMC26 and WMC42 reveal that these compounds inhibited both the integration and disintegration steps in an in vitro experiment which utilized the full released by the dying cells (Weislow et al., *J. Natl. Cancer Inst.* 81:577–586, 1989). An effective antiviral drug is able to protect the infected cells from cytotoxicity by inhibiting some vital function of the virus. Thus an in vitro demonstration of antiviral activity depends on dose-dependent protection of the cytopathic effects of the virus by the putative drugs. FIGS. 4 and 5 show the cytoprotective activity of WMC26 and WMC42. Since many drugs can also be toxic to cells in their own right, a parallel experiment is carried out wherein uninfected cells are treated with the drugs until a concentration is reached where the cells are killed by the action of the drug. These data are indicated on FIGS. 6 and 7. Clearly, both of these drugs were able to protect the infected lymphocytes at concentrations far lower than those which resulted in drug induced killing. This means that the compounds had very good therapeutic indices in this assay.

Figure 8:
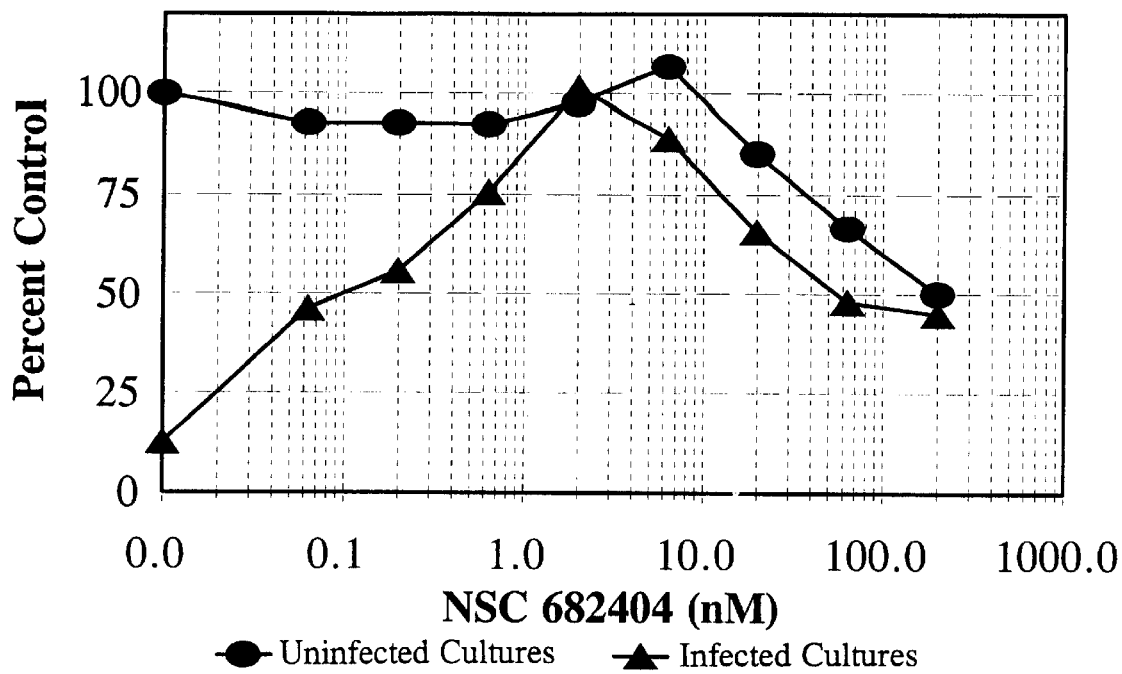
FIG. 8. Inhibition of HIV replication (NSC-682404).
Figure 9:
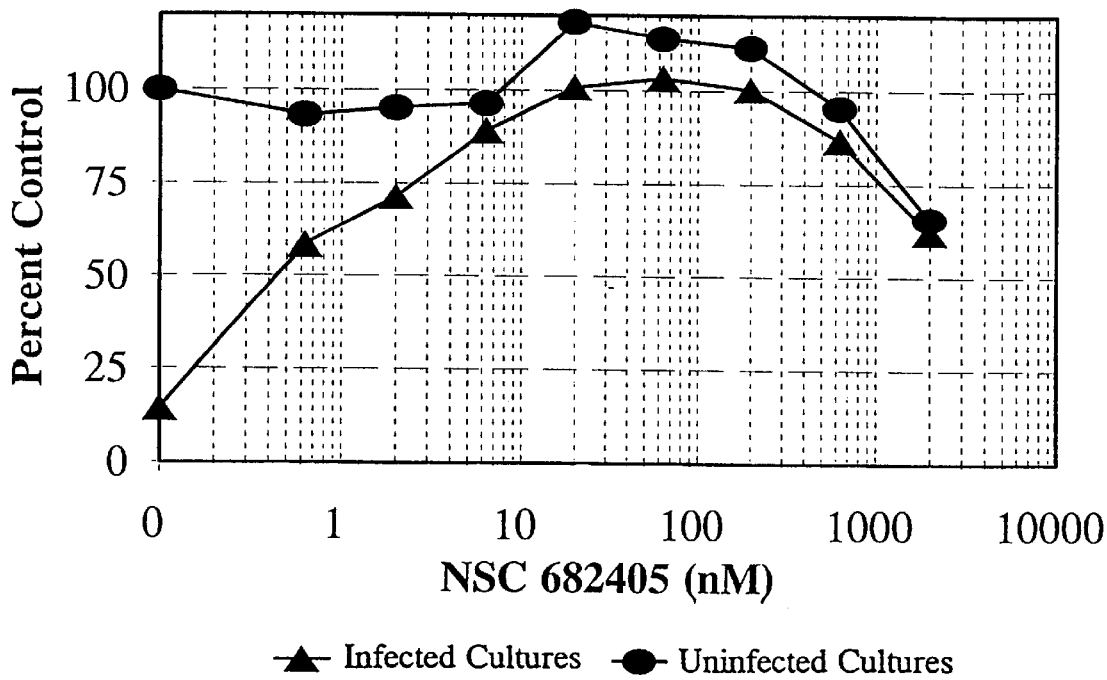
FIG. 9. Inhibition of HIV replication (NSC-682405).

As a result of these preliminary data, additional experiments were carried out to establish the antiviral activity in other cell lines, using a variety of protocols. The preliminary experiments in lymphocytes were confirmed using infected macrophages. Much more extensive experiments were carried out in HIV-1-infected CEM SS leukemia cells. Unfortunately, compounds such as WMC26 are very potently (nanomolar levels) cytotoxic to leukemia (Cholody et al., *J. Med. Chem.* 55:2338–2245, 1995), and therefore could not be shown to be cytoprotective in this assay. However, two derivatives were found which had low anti-leukemic activity while maintaining high antiviral activity. FIGS. 8 and 9 demonstrate the cytoprotective activity of WMC50 and WHC70, respectively, in this cell line. While both compounds are clearly cytoprotective at very low concentrations, it is clear that WMC-70 is likely to be a better drug because of its superior therapeutic index. Thus, while the concentration wherein WMC-70 inhibits the cytotoxic effect of the virus to 50% (the ECSO value) is less than 1 nanomolar, the drug kills 50% of the cells at greater than micromolar concentrations. This gives a therapeutic index of more than 3 orders of magnitude. The corresponding therapeutic index for WMC50 is about 100–200, which is quite acceptable. Additional experiments were carried out on WMC-70. It was shown that the drug did not inhibit either the HIV protease or the reverse transcriptase, two other important enzymes involved in viral replication. WMC-70 also did not damage the gag protein zinc finger, another structural feature in the virus which is considered to be crucial for viral replication. Interestingly, treatment of the HIV-1 virus itself by the drug appeared to prevent its ability to infect CEM cells. Further, WMC-70 appears to affect post-transcription events in the virus. Treatment of cells in which all of the virus is integrated by the drug, reveals that apparently normal viral gag p55 polyprotein is formed, but it is not processed further, i.e., no p24 can be detected. While the inhibition of integration appears to be the principal mechanism by which this compound exerts its antiviral activity, there are perhaps other mechanisms which are also involved in the therapeutic action of this drug, and by extension, of other antiviral drugs of this class.

Compounds WC-26, WMC-42, WMC-50 and WMC-70 are potent, antiviral agents which have potential activity against HIV infections and against AIDS. ("WMC-70" is also referred to herein as "NSC 682405" or "temacrazine".)

EXAMPLE 3

Antiviral Properties of Test Compounds

The antiviral properties of the WMC series of compounds were evaluated. First, all compounds were tested for their ability to inhibit HIV-1 replication in cell culture using the XTT cytoprotection assay. This assay measures the concentration-dependent capacity of compounds to protect CEM-SS cells from the cytopathic effects of HIV-LR. The concentration of compound providing 50% protection is the $EC_{50}$ antiviral value, while the concentration of compound that results in 50% cell death is the $IC_{50}$ toxicity value. As shown in Table 1, compounds NSC 682401–682403 were inactive, indicating that no antiviral effect was observed in the absence of toxicity. NSC 682404 exhibited an $EC_{50}$= 0.41 nM and an $IC_{50}$=158 nM, while temacrazine exhibited an $EC_{50}$=1.1 nM and an $IC_{50}$=2.77 $\mu$M (see also FIGS. 8 and 9). Thus, temacrazine was the most efficacious compound in the XTT cytoprotection assay. This conclusion was also reached when the compounds were tested for anti-HIV-1 activity against HIV-$1_{ADA}$ in human monocyte/macrophage cultures (Table 1).

EXAMPLE 4

Mechanistic Properties of Test Compounds

Figure 10:
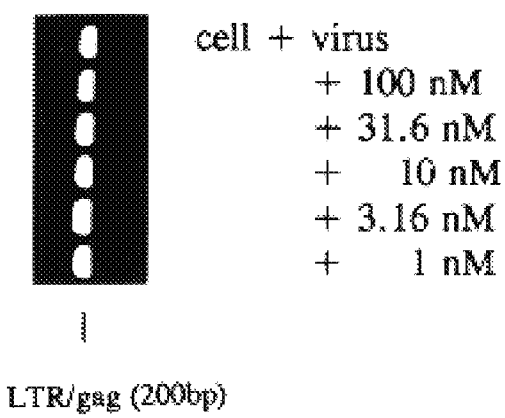
FIG. 10. Inability of NSC 682405 ("temacrazine") to prevent the formation of proviral DNA by reverse transcription.

Data from mechanistic studies against the known antiviral targets of HIV-1 are also shown in Table 1. The compounds did not inhibit attachment of HIV-1 to host cells, the enzymatic activities of HIV-1 reverse transcriptase or protease, or the p7 nucleocapsid protein zinc fingers. Based on the findings thus far our efforts have focused on biological assays of the temacrazine congener. In a time course assay the temacrazine did not prevent the formation of proviral DNA that occurs during reverse transcription, as shown by the amplified LTR/gag region of the proviral DNA (FIG. 10). Temacrazine inhibited 3'-processing and stand transfer activity in an in vitro assay using purified oligomers and recombinant HIV-1 integrase in a concentration dependent manner with an $EC_{50}$ between 10 and 100 nM (Table 1A).

These findings are consistent with temacrazine acting as an inhibitor of HIV-1 integrase, as the proviral DNA formation is completed prior to the integration event during the HIV-1 replication cycle. Experimental compounds that inhibit virus attachment and fusion (e.g. dextran sulfate) and compounds that inhibit reverse transcription (DDC, AZT, Nevirapine, etc.) prevent formation of proviral DNA in the time course assay.

TABLE 1

| Com- | [a]XTT Assay (mM) | | Mo/Mφ (nM) | | [b]Attachment $ID_{50}$ ($\mu$M) | RT $ID_{50}$ ($\mu$M) | [c]p7NC Zinc Finger $ID_{50}$ ($\mu$M) |
|---|---|---|---|---|---|---|---|
| pound | $EC_{50}$ | $IC_{50}$ | $EC_{50}$ | $IC_{50}$ | | | |
| 682401 | Inactive | | 50 | 1000 | $NI_{100\mu M}$ | $NI_{100\mu M}$ | NI |
| 682402 | Inactive | | 160 | 10000 | $NI_{100\mu M}$ | $NI_{100\mu M}$ | NI |
| 682403 | Inactive | | ND | | $NI_{\mu M}$ | $NI_{100\mu M}$ | NI |
| 682404 | 0.41 | 158 | 100 | 10000 | $NI_{100\mu M}$ | 35 | NI |
| 682405 | 1.1 | 2767 | 10 | 10000 | $NI_{100\mu M}$ | $NI_{100\mu M}$ | NI |

[a]The XTT cytoprotection refers to data from the screening assay.
[b]Mechanistic studies for virion attachment, RT and protease were performed as previously described. The values represent $ID_{50}S$, which reflect the concentration that inhibited the indicated activity by 50%.
[c]The p7NC ZF assay measured the percent reduction in relative fluorescence units (RFU) of the zinc finger after treatment of the p7NC protein with 25 $\mu$M of each compound for 10 min.
[d]The "Inactive" indicates that the compound demonstrated no efficacy in the screen.
[e]The "NI" reflects no inhibition of activity at the indicated high test concentration.

TABLE 1A

Mechanism of action studies for Temacrazine

| | $I_{50}(\mu M)^1$ | |
|---|---|---|
| Molecular target | Temacrazine | Control compound |
| Attachment | N[4] | 1.1 µM (Farmatalia) |
| gp 120-CD4 | NI | 4.3 µM (Farmatalia) |
| RT Enzyme Activity | | |
| rAdT Template/primer | NI | 27 nM (A2TTP) |
| rCdG Template/primer | NI | 6 nM (UC38) |
| Protease activity | | |
| HPLC-based assay | NI | 3 nM (KNI-272) |
| Pr55$^{gag}$ processing | NI | 1–10 nM (KNI-272) |
| Integrase | 0.01 to 0.1 | 0.5 µM (ISIS 5320) |
| NCp7[5] | | |
| TSQ (Increase in RFU/90 min) | NI | 17 (NSC 624151) |
| Trp$^{37}$ (Decrease in RFU/10 min) | NI | 145 (NSC 624151) |

[1]$I_{50}$ are the drug concentrations inhibiting 50% of the indicated activity.
[2]Positive controls for individual assays were; Attachment: Farmatalia IC$_{50}$ 1.1 µM (D.J. Clanton et al., J. Acquir. Immune Defic. Syndr. 5:771 (1992)), Reverse transcriptase inhibition: rAdT Template/primer-AZTTP 27 nM, rCdG Template/primer-UC38 6 nM (J.P. Bader et al., Proc. Natl. Acad. Sci. USA, 88:6740 (1991)), protease inhibition (HPLC Detection of cleavage of the Ala—Ser—Glu—Asn—Tyr—Pro—Ile—Val—Glu-amide substrate): KNI-272 nM (S. Kageyama et al., Antimicrob. Agents Chemother, 37:810 (1993)) Integrase inhibitor, ISIS 5320 (R.W. Buckheit, Jr., et al., AIDS Res. Hum. Retrovir. 10:1497 (1994)) and NCp7 Zn$^{2+}$ ejection NSC 625151, (Dithiane) (W.G. Rice, et al., Antimicrob. Agents and Chemother, 41 In Press (1997))
[3]Attachment of HIV-1$_{RF}$ to CEM-SS cells with attachment determined by determination of the amount of cell-bound p24 by p24 ELISA assay of cellular lysates.
[4]NI indicates no inhibition at the high test concentration.
[5]Changes are expressed as relative fluorescence units per unit time.

EXAMPLE 5

Effects of Temacrazine on the Late Phase of the HIV-1 Replication Cycle

Figure 12:
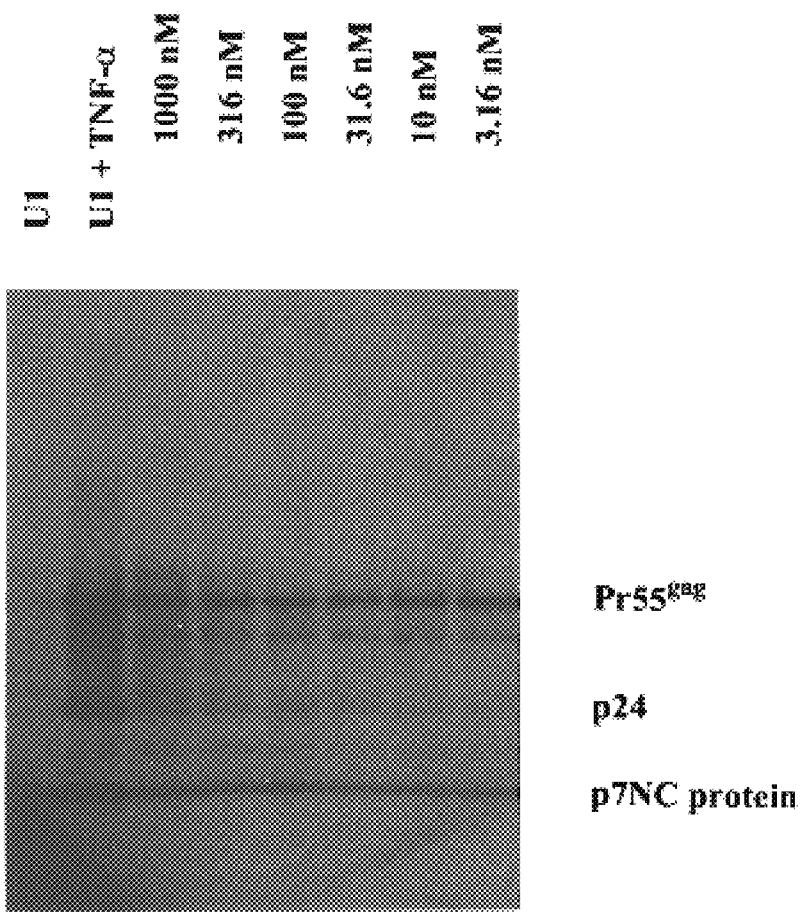
Figure 11:
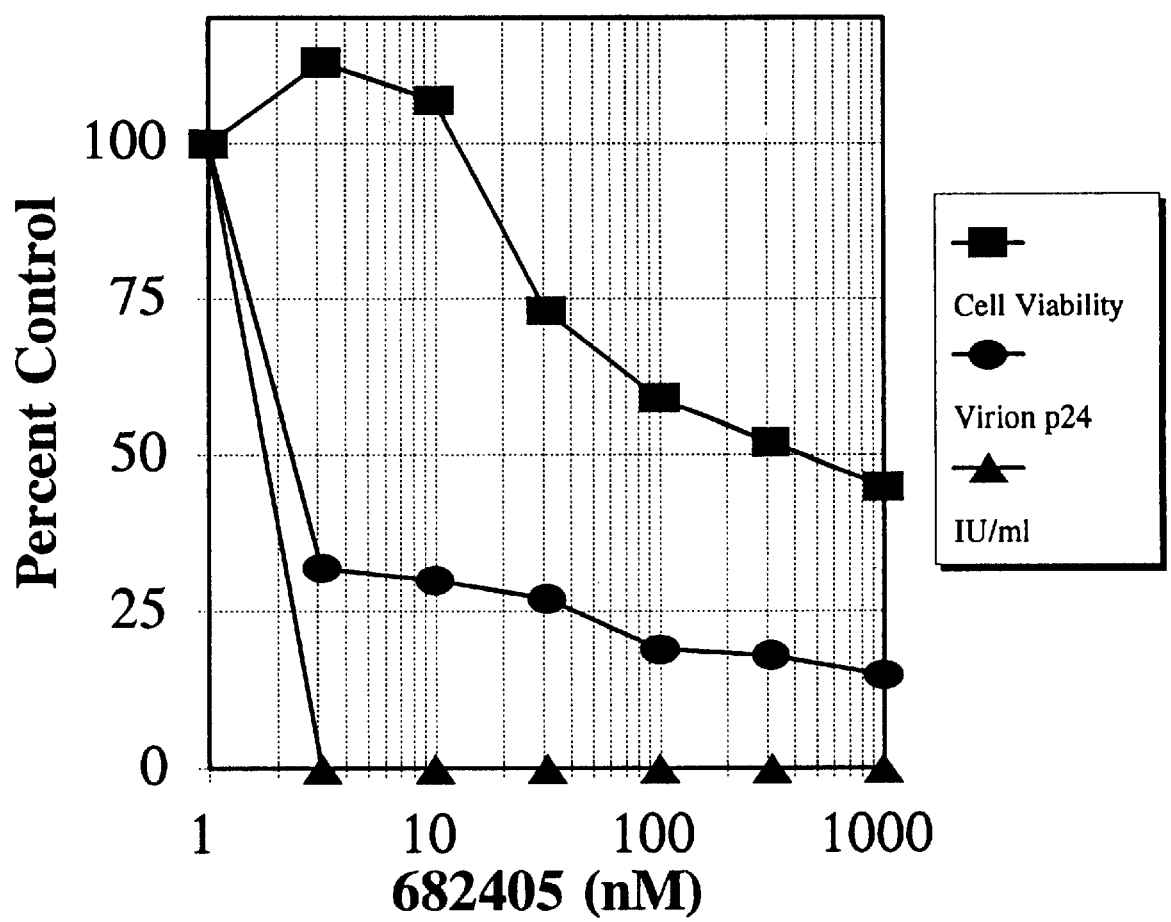

As a model of the late phase events during the HIV-1 replication cycle, U1 cells were used that are latently infected with two copies of HIV-1 proviral DNA. The high level expression of virus production in these U1 cells can be stimulated by certain factors, such as TNF-α. U1 cells were stimulated with TNF-α for 24 hours, after which were added various concentrations of temacrazine, and the cultures were allowed to incubate for 48 additional hours. At that time, the cells were evaluated for viability and for their content of viral protein synthesis and processing, while the cell-free supernatant was evaluated for viral p24 content and for the infectious titer of released virions. FIG. 11 shows that the virus production (p24) was inhibited at concentrations below 4 nM, and that the released viral particles were non-infectious (expressed as infectious units per ml, "IU/ml"). Cell viability was diminished above 30 nM with these U1 cells. Interestingly, inspection of the viral proteins by Western blotting with p7 and p24 antisera (FIG. 12) revealed that the Gag precursor polyprotein (Pr$_{gag}$) was synthesized but was not processed by the HIV-1 protease into mature viral proteins (p24 and p7NC).

In a similar study, cells were either treated for 24h with TNFA followed by the addition of temacrazine, or temacrazine and TNFA were added simultaneously, or temacrazine was added 24 h post TNFα addition. After TNFα induction and temacrazine treatment, cultures were continued for 72 h after which virion-associated p24 and cell viability (XTT dye reduction) were measured. Temacrazine was an efficient inhibitor of HIV-1 virus replication in both U1 (and also the latently infected cell line, ACH-2) with an EC$_{50}$ in the 10 to 100 nM range. In addition, temacrazine-mediated virus inhibition was not significantly effected by the order of addition of temacrazine and TNFα.

Also, it was found that a 30 min. pulse of cultures with temacrazine presented subsequent production of infectious virus following stimulation with TNFα.

EXAMPLE 6

Direct Inactivation of HIV-1 by Teancrazine

Figure 13:
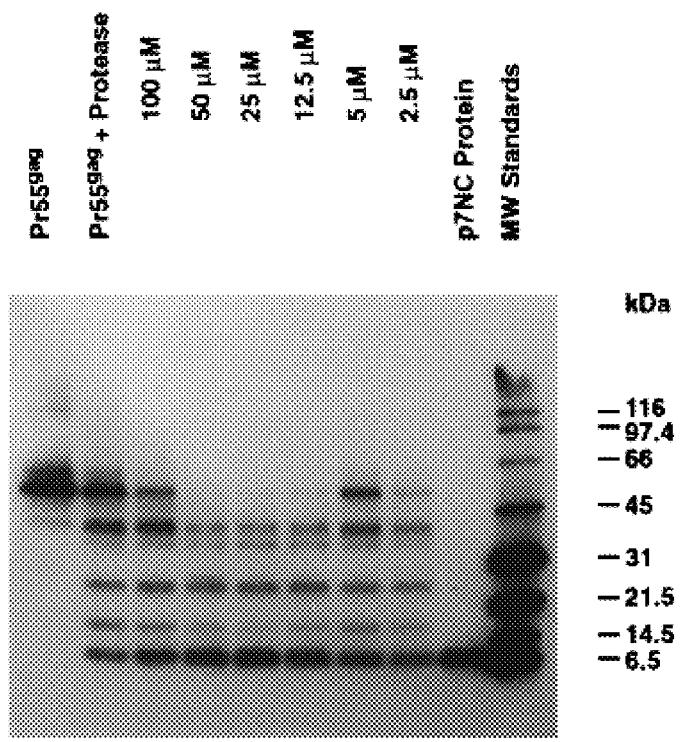

The mechanistic studies in Table 1 indicated that the compound did not inhibit HIV-1 protease activity. However, to insure that the HPLC-based assay (used in Table 1) was providing accurate findings, the action of temacrazine in the Gag processing assay was evaluated. In this assay, purified recombinant HIV-1 protease enzyme was pretreated with the test reagent for one hour at 37° C., and then exposed the recombinant Pr55$^{gag}$ precursor polyprotein to the treated enzyme. As shown in FIG. 13, the protease alone was able to efficiently process the precursor. In addition, pretreatment of the enzyme with the compound had no inhibitory effect. Together, these findings demonstrated that temacrazine does not inhibit the HIV-1 protease enzyme.

Significance of Findings

Temacrazine demonstrated potent anti-HIV-1 activity in models of acute infection against lymphocytotropic HIV-1 strains in proliferating cells and against monocytotropic HIV-1 strains in non-proliferating normal cells. Moreover, the compound exerted an antiviral effect on previously infected cells. The exact nature of the late phase effect is under investigation. Nevertheless, temacrazine potently inhibited the production of new infectious virus from previously infected cells. This is a very important action of the compound given that any means for reducing the viral burden in HIV-1 infected persons would result in decreases in subsequent rounds of infection in vivo. In addition, the ability of the compound to directly inactivate virions would be of great significance, since this would effectively reduce the infectious titer in plasma and prevent later rounds of replication and seeding of the virus.

EXAMPLE 7

Figure 14:
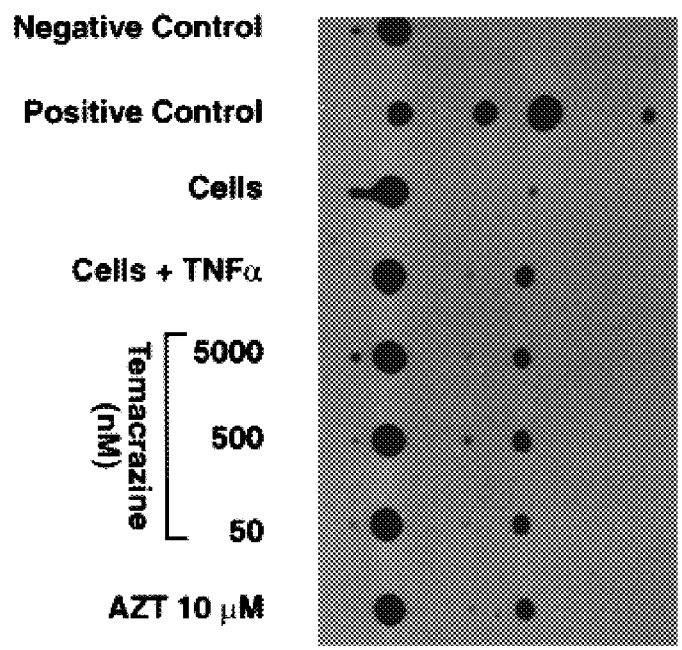

Initiation and regulation of HIV-1 transcription requires a complex series of interactions with cellular transcription factors, such as NFkB, SP-1 and AP-1, and the participation of cellular factors in the transcriptional complex. In addition, the post-integrative model used here requires TNFA stimulated U1 and ACH-2 cells, this model requires not only the participation of the NFKB transcriptional complex, and also components of the TNFα signaling pathway. In order to rule out that temacrazine was non-specifically effecting transcription or down-regulating replication by interfering with the TNFα signal pathway, LTR-directed chloramphenicol acetyltransferase (CAT) activity was measured in BF-24 cells. BF-24 cells are derived from the THP-1 monocytic cell line and carry a stably integrated CAT gene under the transcriptional control of the HIV-1 LTR (S. Schwartz, et al., Proc. Natl. Acad. Sci. USA 86:7200 (1989); B. K. Felber, et al., Science 239:184 (1988)). The LTR in this monocytic cell line is inducible by IL-6, PMA and TNFα, and produces enzymatically active chloramphenicol transferase ("CAT"). Induction of CAT enzyme activity by TNFP occurs in the absence of any viral components, and as a result will identify mechanisms of action that are virus regulatory protein independent. BF-24 cells were stimulated with TNFA and treated with temacrazine for 24 h, and cellular proteins were then collected for determination of CAT enzyme activity (FIG. 14).

CAT activity was determined using a fluorescent Bodipy conjugated chloramphenicol after 18 h of reaction with 50 µg of protein extract containing Acetyl CoA. FIG. 14 shows that BF-24 cells alone have a low intrinsic CAT activity that is inducible by at least 10 fold by TNFα. Treatment of BF-24 cells with up to 5 µM temacrazine did not significantly alter CAT induction. Similarly, AZT which does not effect temacrazine's activity because reverse transcription is not required for CAT expression, was inactive. Even though, these data argue against a non-specific transcriptional/translational effect, specific experiments were conducted to verify this hypothesis. The incorporation of $^3$H Leucine (to measure protein metabolism), $^3$H Thymidine (to measure DNA replication) and $^3$H Uridine (to measure RNA production) in CEM-SS cells was determined and it was found that temacrazine had no effect on these cellular parameters. These data strongly suggest that the antiviral activity of temacrazine is not due to a non-specific downregulation of transcription, and requires the participation of viral factor(s).

EXAMPLE 8

Figure 15:
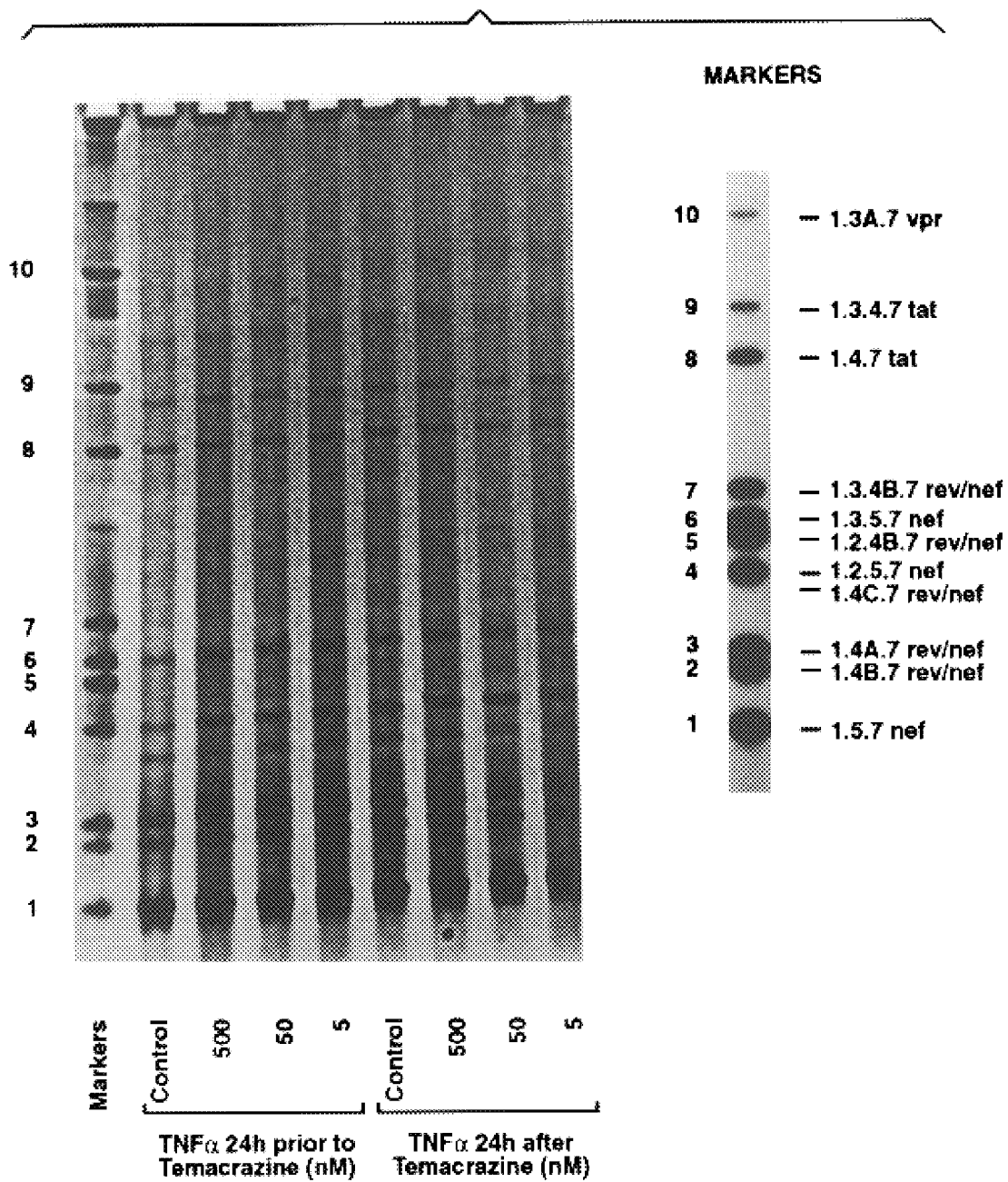

Temacrazine completely inhibited the expression of unspliced or singly spliced mRNA at 500 and 50 nM when given either prior to or 24 h after the TNFα induction. Similar results were seen when temacrazine and TNFα were added simultaneously. In contrast, temacrazine did not alter the expression of HIV-1 multispliced transcripts when using RT-PCR primers designed to detect all multi-spliced rev independent mRNAs (FIG. 15).

As a control the house keeping gene porphobilinogen deaminase (Hydroxymethylbilane synthase, "PBGD") was amplified to determine uniformity of loading. Since the drug did not decrease PBGD expression, this demonstrates that temacrazine did not non-specifically downregulate transcription.

EXAMPLE 9

Figure 16:
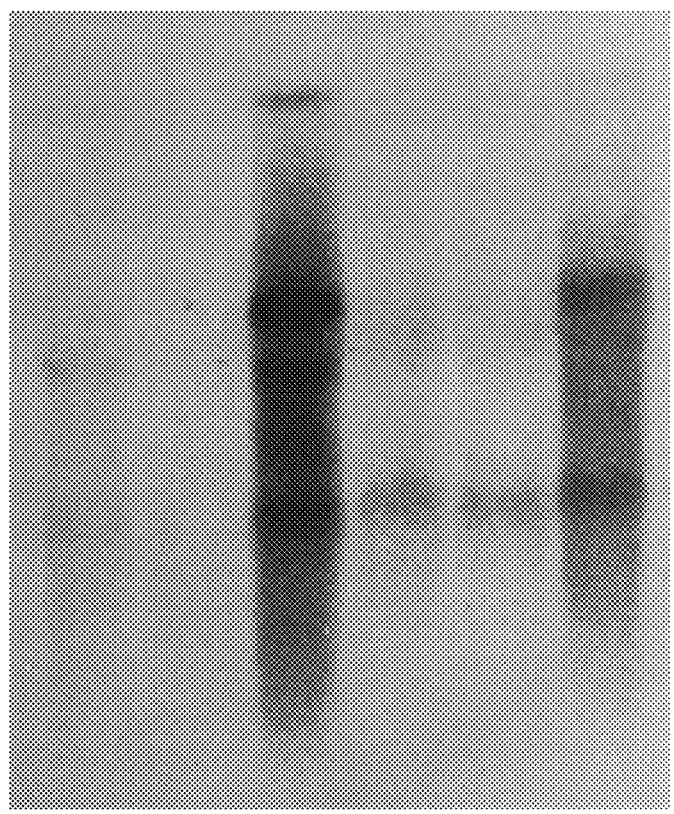

To assess the possibility that temacrazine was regulating HIV-1 mRNA expression, the expression of total HIV-1 mRNA by Northern blotting was examined (FIG. 16).

FIG. 16 shows that upon stimulation with TNFα, HIV-1 specific mRNA expression in U-1 cells increases dramatically. Treatment of TNFα stimulated U-1 cells with 10 and 100 nM temacrazine suppressed mRNA production globally, generating a phenotype that is very close in appearance to that of the unstimulated U1 cells ("rev" independent phenotype). However, treatment with 1 nM temacrazine resulted in a decrease in single spliced and unspliced mRNA with no apparent decrease in the multi-spliced mRNA. These patterns of RNA inhibition suggest that temacrazine is inhibiting or altering the expression of rev-responsive element (RRE) containing mRNAs.

EXAMPLE 10

In Vivo Data

The novel mechanism of action of temacrazine and its broad range of activity against HIV-1 and its high therapeutic indexes led us to assess its in vivo and anti-viral properties in a nude mouse hollow fiber model of HIV-1 replication. Briefly, CEM-SS cells are infected with HIV-$1_{RF}$ and placed into hollow fibers and implanted intraperitoneal or subcutaneously into nude mice. Temacrazine in a DMSO vehicle was intraperitoneally administered either 3×, 2× or 1× per day with total dosage of 25 mg/kg per day for 6 days. Similarly, mice are being treated by oral and intravenous administration of temacrazine. Peritoneal washes and serum samples were collected and p24 expression determined by antigen capture. The results are shown in Table 2. Intraperitoneal administration of temacrazine reduced the amount of detectable p24 in peritoneal washes by 5 to 10 fold independently of the dosage schedule. Temacrazine also reduced the amount of p24 in the serum. Thus, temacrazine reduces HIV-1 replication in vivo.

Experiments presented herein indicate that temacrazine functions by interacting with a post-integrative event in the HIV life cycle in infected cells. This interaction leads to the loss of viral transcripts with a selective depletion of unspliced and singly spliced transcripts. This drug functions by a new mechanism of antiviral action. Nevertheless, the utility of temacrazine and its congeners as potential antivirals is further strengthened by the ability of temacrazine to inhibit HIV-1 replication in an in vivo model.

TABLE 2

In Vivo activity of temacrazine in the hollow fiber mouse model

| Treatment[2] | Animals | Peritoneal Wash (pg p24) | | | Serum (pg p24) | | |
|---|---|---|---|---|---|---|---|
| | | mean | SD | p[1] | Mean | SD | P |
| uninfected | 3 | 0 | 0 | — | 0 | 0 | — |
| Saline q8h[3] | 5 | 2185 | 675 | — | 2694 | 717 | — |
| DMSO q8h | 5 | 2451 | 868 | — | 3716 | 1287 | — |
| ddC 40 mg/Kg q8h | 3 | 7 | 12 | 0.002[4] | 87 | 21 | 0.0009 |
| Temacrazine | | | | | | | |
| 8.5 mg/kg q8h | 2 | 460 | 396 | 0.026 | 1790 | 198 | 0.1 |
| 12.5 mg/kg q12h | 3 | 190 | 97 | 0.004 | 1863 | 601 | 0.06 |
| 25 mg/kg q24h | 3 | 593 | 250 | 0.002 | 2030 | 903 | 0.q1 |

Nude mice were implanted with hollow fibers containing HIV-$1_{RF}$ infected peripheral blood mononuclear cells and dosed with temacrazine (total dose 25 mg/kg).
[1]Students t-test.
[2]All compounds were given intraperitoneally.
[3]q is frequency of dosage.
[4]Groups significantly different from animals injected with DMSO alone.

All publications mentioned in the present application are hereby incorporated by reference in their entirety.

While the foregoing invention has been described in some detail for purposes of clarity and understanding, it will be appreciated by one skilled in the art from a reading of the disclosure that various changes in form and detail can be made without departing from the true scope of the invention.

We claim:

1. A compound having the formula (I):

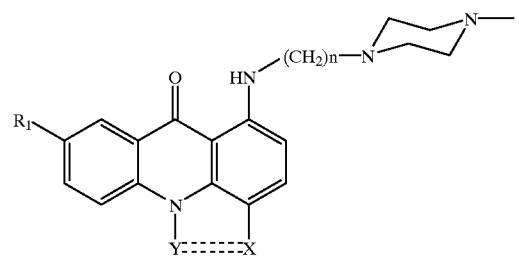

-continued

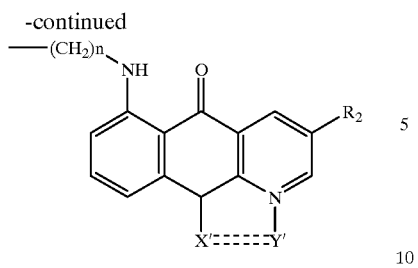

wherein

R1 and R2 are independently —H, —OH, amino, $C_1$–$C_8$ alkylamino, $C_1$–$C_8$ dialkylamino, $C_1$–$C_8$ alkoxy, $C_1$–$C_8$ alkyl, $C_1$–$C_8$ haloalkyl or halogen;

n is 2 to 6;

X and X' are independently —N or —$NO_2$;

Y and Y' are independently —N or —CH, or —H; and double-slash represents a double bond or no bond; such that when X or X' is —N, Y or Y' is —CH or —N, and the double-slash is a double bond, and when X or X' is —$NO_2$, Y or Y' is —H, and the double slash is no bond.

2. The compound according to claim 1 wherein the compound is:

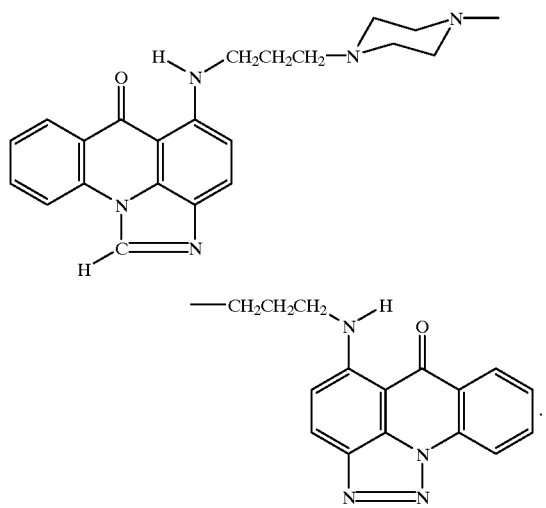

3. The compound according to claim 1 wherein the compound is:

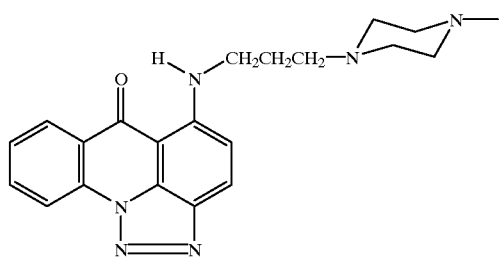

-continued

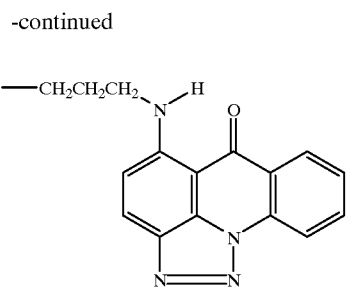

4. A pharmaceutical composition comprising a compound according to claim 1 and a pharmaceutically acceptable carrier.

5. A method of inhibiting neoplastic cell growth comprising: administering an effective amount of a compound having the formula:

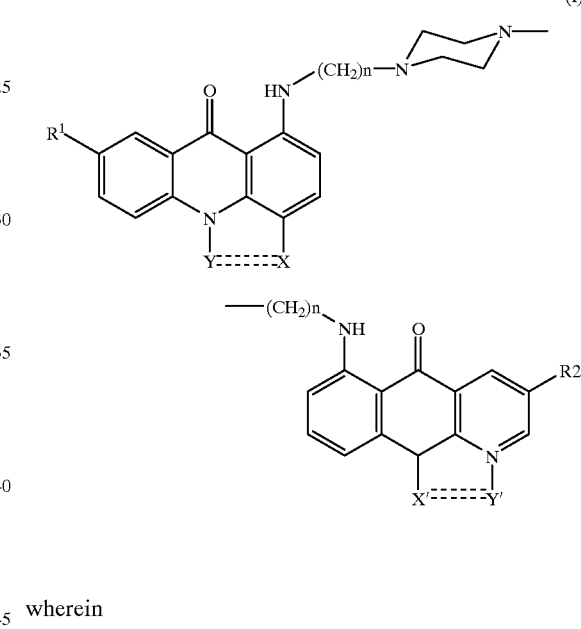

(I)

wherein

R1 and R2 are independently —H, —OH, amino, $C_1$–$C_8$ alkylamino, $C_1$–$C_8$ dialkylamino, $C_1$–$C_8$ alkoxy, $C_1$–$C_8$ haloalkyl or halogen;

n is 2 to 6;

X and X' are independently —N or —$NO_2$;

Y and Y' are independently —N or —CH, or —H; and double-slash represents a double bond or no bond; such that when X or X' is —N, Y or Y' is —CH or —N, and the double-slash is a double bond, and when X or X' is —$NO_2$, Y or Y' is —H, and the double slash is no bond.

* * * * *

UNITED STATES PATENT AND TRADEMARK OFFICE
CERTIFICATE OF CORRECTION

PATENT NO. : 6,187,775 B1
DATED : February 13, 2001
INVENTOR(S) : Christopher J. Michejda, Marek W. Cholody, William G. Rice, and James A. Turpin Page 1 of 1

It is certified that error appears in the above-identified patent and that said Letters Patent is hereby corrected as shown below:

The second named inventor should read "W. Marek Cholody."

Signed and Sealed this

Twenty-seventh Day of November, 2001

Attest:

NICHOLAS P. GODICI
*Attesting Officer*     *Acting Director of the United States Patent and Trademark Office*